US006890293B2

(12) United States Patent
Kobayashi

(10) Patent No.: US 6,890,293 B2
(45) Date of Patent: May 10, 2005

(54) DRIVING APPARATUS FOR MASSAGING DEVICE FOR SEXUAL ORGANS

(75) Inventor: Takehiro Kobayashi, Kanagawa (JP)

(73) Assignee: Sunworld Corporation, Tokyo (JP)

( * ) Notice: Subject to any disclaimer, the term of this patent is extended or adjusted under 35 U.S.C. 154(b) by 54 days.

(21) Appl. No.: 10/390,310

(22) Filed: Mar. 17, 2003

(65) Prior Publication Data

US 2003/0191362 A1 Oct. 9, 2003

(30) Foreign Application Priority Data

Apr. 1, 2002 (JP) ....................................... 2002-098176

(51) Int. Cl.[7] ................................................... A61F 5/00
(52) U.S. Cl. .......................................... 600/38; 128/845
(58) Field of Search ............................. 600/38; 128/845

(56) References Cited

U.S. PATENT DOCUMENTS

| | | |
|---|---|---|
| 3,874,373 A | 4/1975 | Sobel |
| 4,059,100 A | 11/1977 | Glage |
| 4,580,553 A | 4/1986 | Laib |
| 4,722,327 A | 2/1988 | Harvey |
| 4,790,296 A | 12/1988 | Segal |
| 5,076,261 A | 12/1991 | Black |
| 6,142,929 A | 11/2000 | Padgett |

FOREIGN PATENT DOCUMENTS

| | | |
|---|---|---|
| JP | 2002028210 A | 1/2002 |

*Primary Examiner*—John P. Lacyk
(74) *Attorney, Agent, or Firm*—Boyle Fredrickson Newholm Stein & Gratz S.C.

(57) ABSTRACT

A driving apparatus of a massaging device for sexual organs comprises a pedestal, a driving device fixed detachably on the pedestal, and moving means provided on the driving device, to which a massaging device for sexual organs is attached. The moving means is moved reciprocally linearly, and vertically substantially, and the massaging device is for male sex organs. The moving means is moved reciprocally linearly, and obliquely substantially, and the massaging device is for female sex organs. A motion of lateral direction is added to the moving means so as to move the moving means along an endless loop.

13 Claims, 4 Drawing Sheets

DRIVING APPARATUS FOR MASSAGING DEVICE FOR SEXUAL ORGANS

BACKGROUND OF THE INVENTION

1. Field of the Invention

The present invention relates to a driving apparatus of massaging device for sexual organs, and more particularly to a driving apparatus of massaging device for sexual organs usable for both of female sex organs and male sex organs.

2. Description of the Prior Art

A conventional massaging device for sexual organs has been disclosed in the Japanese Patent Application Laid-Open No. 28210/2002.

However, in such conventional massaging device, it is necessary to hold and drive the massaging device by the hand of user, so that the user is tired with the work. Further, such conventional massaging device cannot be use for both of female sex organs and male sex organs.

SUMMARY OF THE INVENTION

An object of the present invention is to solve the aforesaid problematic points in the prior art, and to provide a driving apparatus of massaging device for sexual organs.

Another object of the present invention is to obtain a driving apparatus of massaging device for sexual organs comprising a pedestal, a driving device fixed detachably on the pedestal, and moving means provided on the driving deice, to which a massaging device for sexual organs is attached.

Still another object of the present invention is to provide the driving apparatus, wherein the moving means is moved reciprocally linearly.

Further object of the present invention is to provide the driving apparatus, wherein the moving means is moved vertically substantially, and the massaging device is for male sex organs.

Still further object of the present invention is to provide the driving apparatus, wherein the moving means is moved obliquely substantially, and the massaging device is for female sex organs.

Yet further object of the present invention is to provide the driving apparatus, wherein a motion of a lateral direction is added to the moving means so as to move the moving means along an endless loop.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

DESCRIPTION OF THE PREFERRED EMBODIMENTS

An embodiment of an apparatus according to the present invention will now be explained with reference to the drawings.

Figure 1:
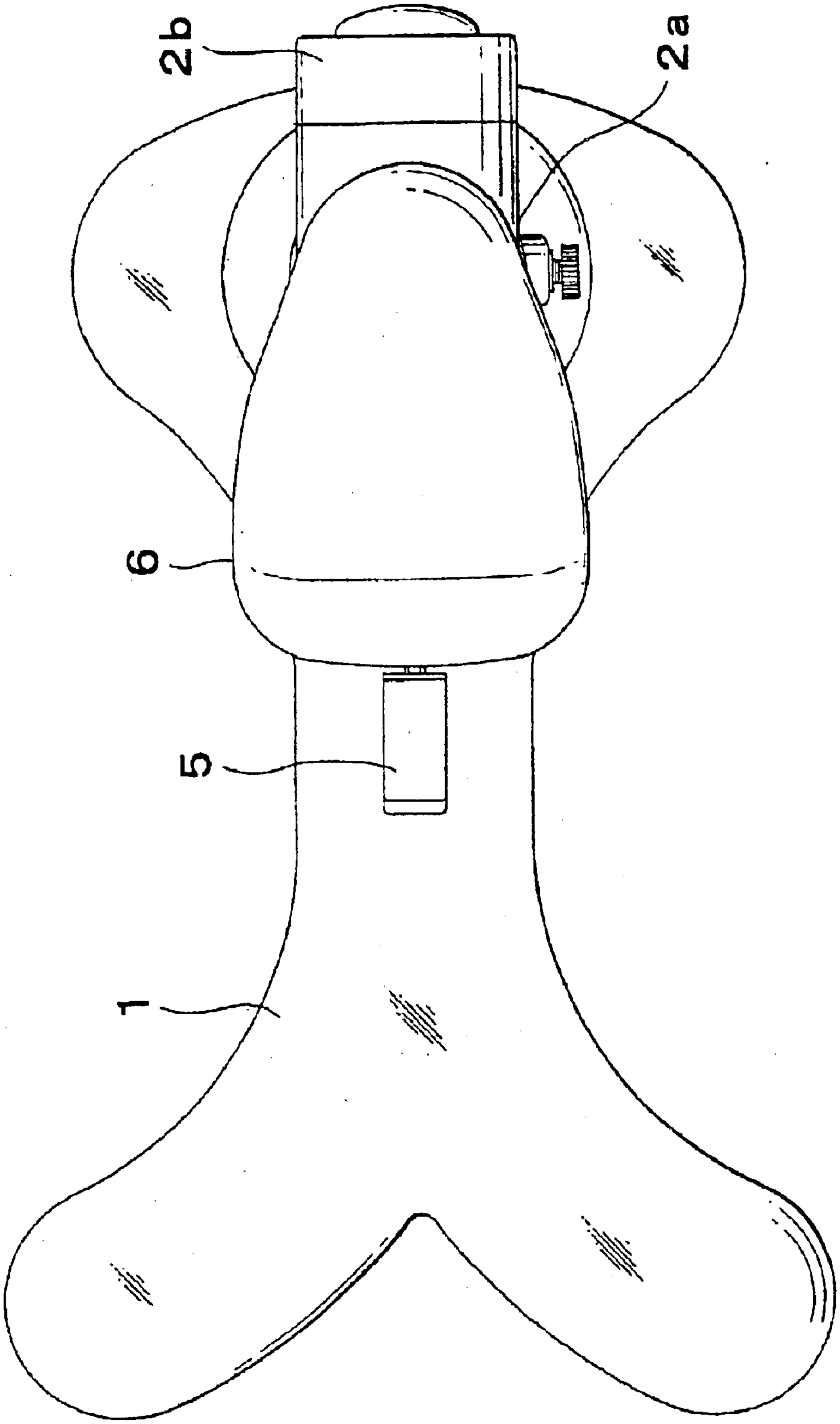
FIG. 1 is a plan view of a driving apparatus of massaging device for sexual organs according to the present invention, which is usable for male sex organs.
Figure 2:
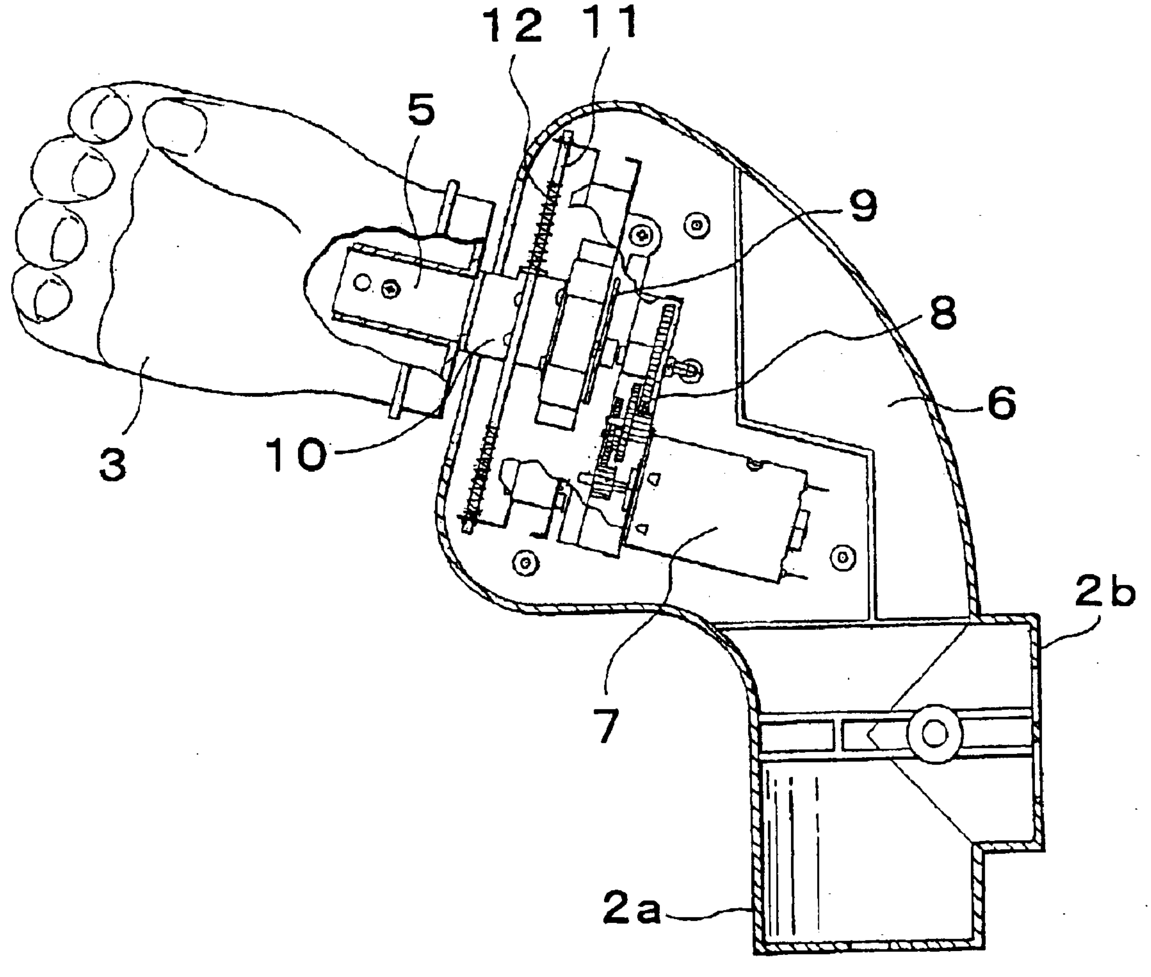
FIG. 2 is a vertically sectioned front view of a part of the driving apparatus shown in FIG. 1 with a massaging device for male sex organs, in the in-use position.

A driving apparatus of massaging device for sexual organs according to the present invention comprises, as shown in FIG. 1 and FIG. 2, a pedestal 1 of planar plate on which a hip of user is set, and a driving device 6. The driving device 6 has fixing portions 2*a* and 2*b* formed at lower portions thereof, either of which is fixed detachably on the pedestal 1, and moving means 5 provided at an upper portion thereof for holding detachably a massaging device 3 for male sex organs or a massaging device 4 for female sex organs.

The driving device 6 further comprises, as shown in FIG. 2, a motor 7, a conventional rotary cam 9 connected to the motor 7 through gear trains 8 for converting a rotary motion of the motor 7 to a linear reciprocating motion, a driving member 10 moved reciprocally linearly by the rotary cam 9, a guide rod 11 for holding movably the driving member 10, and a return spring 12 wound around the guide rod 11 for retuning the driving member 10.

In case that the fixing portion 2*a* of the driving device 6 is fixed on the pedestal 1, as shown in FIG. 1 and FIG. 2, the moving means 5 is moved along a line extending vertically substantially with respect to the upper surface of the pedestal 1. In this case, as shown in FIG. 2, the massaging device 3 for male sex organs is attached to the moving means 5.

Figure 3:
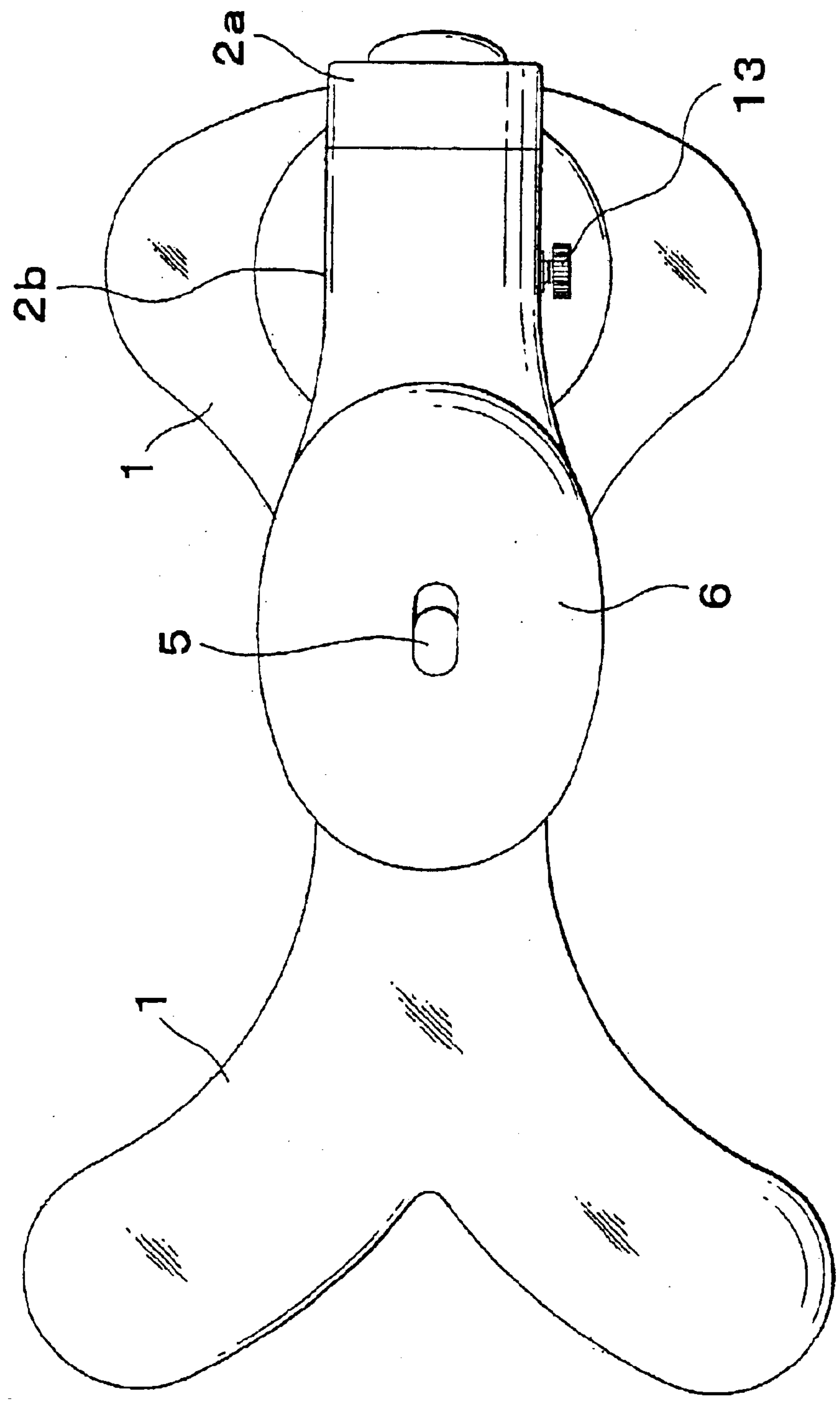
FIG. 3 is a plan view of a driving apparatus according to the present invention, which is usable for female sex organs.
Figure 4:
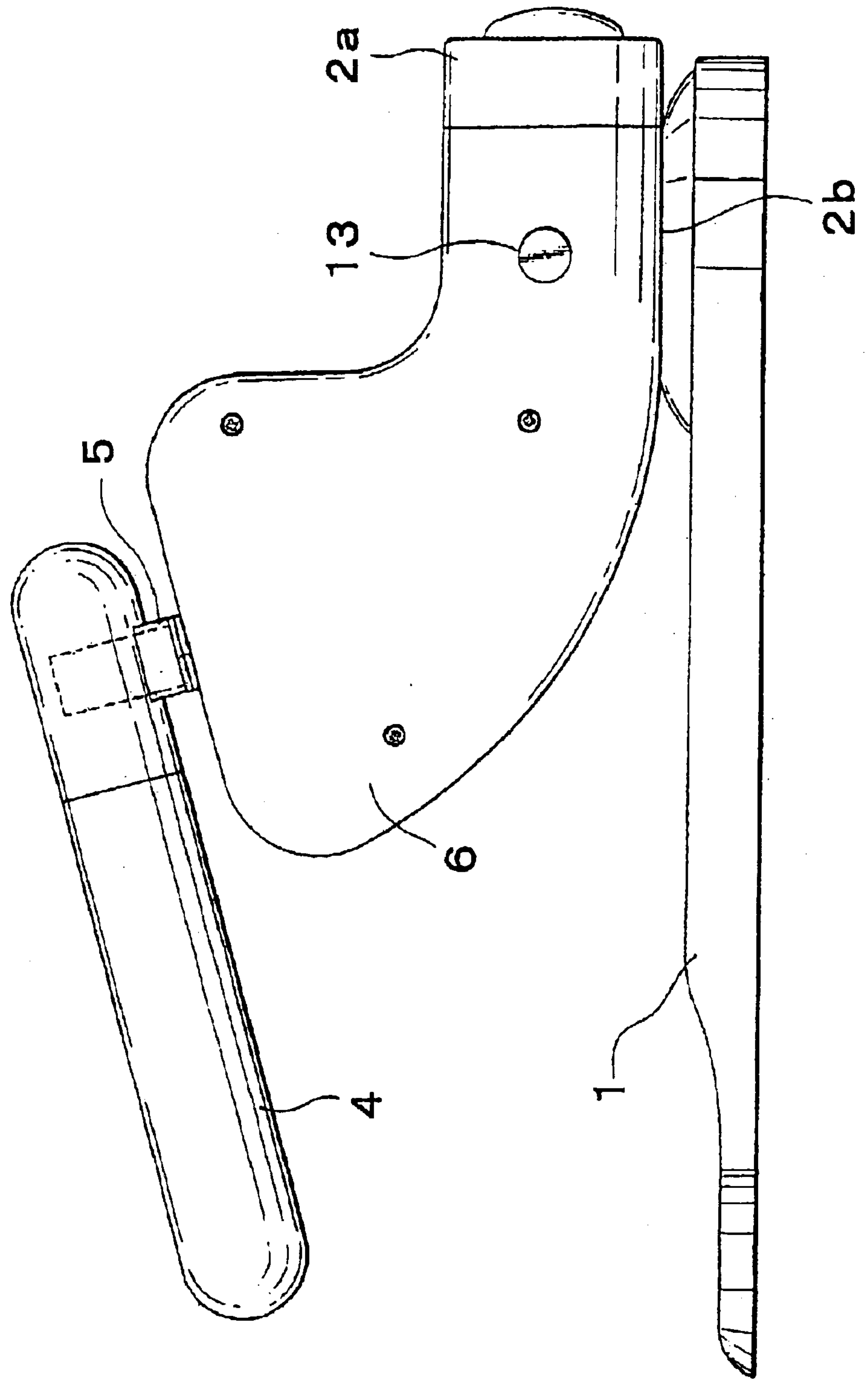
FIG. 4 is a front view of the driving apparatus shown in FIG. 3 with a massaging device for female sex organs, in the in-use position.

On the contrary, in case that the fixing portion 2*b* of the driving device 6 is fixed on the pedestal 1, as shown in FIG. 3 and FIG. 4, the moving means 5 is moved along a line extending obliquely substantially with respect to the upper surface of the pedestal 1. In this case, as shown in FIG. 4, the massaging device 4 for female sex organs is attached to the moving means 5.

It is preferable to adjust a height or a distance between the upper surface of the pedestal 1 and the massaging device 3 or 4.

It is also preferable to change the rotary speed of the motor 7 through a suitable control circuit (not shown) in order to change the stroke and/or the moving speed of the massaging device 3 or 4.

It may be possible to move the moving means 5 along an endless loop such as a numeral character of eight by applying a motion of lateral direction to the moving means 5 by exchanging the rotary cam 9.

As stated above, according to the driving apparatus of massaging device for sexual organs of the present invention, the driving device 6 is held stationary by the pedestal 1 when the user sits on the pedestal 1, so that the massaging device can be held stably and operated easily. Further, the driving apparatus according to the present invention can be used for both of the massaging device 3 for male sex organs and the massaging device 4 for female sex organs, by changing the direction and the position of the driving device 6.

While this invention has been described with specific embodiments thereof, it is evident that many alternatives, modifications, and variations will be apparent to those skilled in the art. Accordingly, the preferred embodiments of the invention as set forth herein are intended to be illustrative, not limiting. Various changes may be made without departing from the spirit and scope of the invention.

What is claimed is:

1. A driving apparatus for a massaging device for sexual organs comprising:

a pedestal, on which a hip of a user is adapted to rest, a driving device having first and second fixing portions which are selectively and alternatively detachably fixable on the pedestal, and a moving device that is provided on the driving device and to which the massaging device for sexual organs is attached, wherein, when the first fixing portion is fixed on the pedestal, the moving device is movable at least substantially obliquely with respect to the upper surface of the pedestal, and wherein, when the second fixing portion is fixed on the pedestal, the moving device is movable at least substantially vertically with respect to the upper surface of the pedestal.

2. The driving apparatus of claim 1, wherein the massaging device is for one of male sex organs and female sex organs.

3. The driving apparatus of claim 1, wherein the moving device is also capable of moving laterally so as to move in an endless loop.

4. The driving apparatus of claim 2, wherein the moving device is also capable of moving laterally so as to move in an endless loop.

5. The driving apparatus of claim 1, wherein the massaging device is a dildo.

6. The driving apparatus of claim 1, wherein the massaging device is an artificial hand configured to slidably receive a penis.

7. In combination:

a massaging device for sexual organs; and a drive device including a pedestal on which a hip of a user is configured to be set, a driving device which can be selectively and removably mounted on the pedestal in first and second orientations, and a reciprocating moving device that is provided on the driving device and to which the massaging device for sexual organs is mounted, wherein, when the driving device is mounted on the pedestal in the first orientation thereof, the moving device is movable at least substantially obliquely with respect to the upper surface of the pedestal, and wherein, when the driving device is fixed on the pedestal in the second orientation thereof, the moving device is movable at least substantially vertically with respect to the upper surface of the pedestal.

8. The combination of claim 7, wherein the driving device has first and second fixing portions which are selectively and alternatively detachably fixable on the pedestal to define the first and second orientations of the driving device, respectively.

9. The combination of claim 8, wherein the massaging device is a first massaging device that is configured to be used when the first fixing portion of the driving device is mounted on the pedestal, and further comprising a second massaging device that is configured to be used when the second fixing portion of the driving device is mounted on the pedestal.

10. The combination of claim 9, wherein the first and second massaging devices are configured to massage female organs and male organs, respectively.

11. The combination of claim 10, wherein the first and second massaging devices are detachably mountable on the moving device in place of one another.

12. The combination of claim 10, wherein the moving device is configured to move through an endless loop having a lateral component through at least part of the loop.

13. The combination of claim 7, wherein the moving device is configured to move through an endless loop having a lateral component through at least part of the loop.

* * * * *